United States Patent [19]

Chan

[11] Patent Number: 5,735,804
[45] Date of Patent: Apr. 7, 1998

[54] MASSAGING FOOT PAD

[76] Inventor: Erik Chan, 255 Bridgeside Cir., Danville, Calif. 94506

[21] Appl. No.: 534,395

[22] Filed: Sep. 27, 1995

[51] Int. Cl.$^6$ ............................... A43B 13/40; A61F 5/14
[52] U.S. Cl. ............... 601/136; 601/28; 601/111; 601/133; 601/134; 36/43; 36/141
[58] Field of Search ................................ 601/28, 79, 83, 601/95, 104, 111, 107, 114, 133, 134, 136, 138, 145-6; 36/43, 44, 141, 71

[56] References Cited

U.S. PATENT DOCUMENTS

| | | | |
|---|---|---|---|
| D. 348,108 | 6/1994 | Kim et al. | D24/212 |
| 2,476,921 | 7/1949 | Shock | 272/57 |
| 3,037,500 | 6/1962 | Daugherty | 128/57 |
| 3,722,113 | 3/1973 | Birkenstock | 36/11.5 |
| 4,003,372 | 1/1977 | Willoby | 601/28 |
| 4,075,772 | 2/1978 | Sicurella | 36/43 |
| 4,249,521 | 2/1981 | Gueret | 128/62 R |
| 4,345,387 | 8/1982 | Daswick | 36/43 |
| 4,383,342 | 5/1983 | Forster | 601/134 X |
| 4,633,858 | 1/1987 | Rutsch et al. | 601/133 |
| 4,685,224 | 8/1987 | Anger | 36/43 |
| 4,733,655 | 3/1988 | Smal | 601/133 |
| 4,831,749 | 5/1989 | Tsai | 36/3 B |
| 5,018,511 | 5/1991 | Yokoi | 601/111 X |
| 5,322,056 | 6/1994 | Menghi et al. | 601/136 |
| 5,365,678 | 11/1994 | Shibata | 36/29 |

FOREIGN PATENT DOCUMENTS

| | | | |
|---|---|---|---|
| 2553997 | 5/1985 | France | 601/136 |
| 1410944 | 10/1975 | United Kingdom | 601/134 |

*Primary Examiner*—Danton D. DeMille
*Attorney, Agent, or Firm*—David Pressman; John S. Heyman

[57] ABSTRACT

A massaging foot pad can be installed in a shoe or on a sandal. It includes resilient protrusions arranged on top of a sheet. The protrusions are elongated in a horizontal direction, and slanted in an orthogonal direction, so that they each include an upper side facing obliquely upwardly, and a lower side facing obliquely downwardly. In one embodiment the protrusions include a notch arranged on a lower side, and a large rounded tip. In another embodiment, the protrusions include a large rounded tip and a narrow base. In still another embodiment, the protrusions include a thin tip, a wide base, and a notch on the lower side. In yet another embodiment, the protrusions include a convex upper side and a convex lower side. In all embodiments, the protrusions easily bend in the direction of slanting when pressed by a foot during the downward movement of a walking step, so that they rub horizontally across the bottom of the foot. When the foot is lifted during the upward movement of the walking step, the protrusions rebound in the opposite direction, so that they rub horizontally across the bottom of the foot backwardly. The to-and-fro movement of the protrusions massage the bottom of the foot as the user walks.

19 Claims, 3 Drawing Sheets

5,735,804

MASSAGING FOOT PAD

BACKGROUND OF THE INVENTION

1. Field of the Invention

This invention relates generally to footwear, specifically to a massaging foot pad.

2. Prior Art

A variety of massaging foot pads and similar devices are known. U.S. Pat. No. 2,476,921 to Shock (1947) shows a massaging foot pad with beads extending orthogonally from a sheet. U.S. Pat. No. 3,037,500 to Daugherty (1960) shows a rolling foot massager that includes round beads extending orthogonally from the surface of a cylinder. U.S. Pat. No. 3,722,113 to Birkenstock (1973) shows a sandal with round bristles of different lengths extending orthogonally from the insole. U.S. Pat. No. 4,075,772 to Sicurella (1978) shows an insole with longitudinally symmetrical ribs. U.S. Pat. No. 4,345,387 to Daswick (1982) shows an insole with hemispherical beads arranged thereon. U.S. Pat. No. 4,685,224 to Anger (1987) shows an insole with longitudinally symmetrical ribs. U.S. Pat. No. 4,831,749 to Tsai (1989) shows an insole with an array of massaging round beads interconnected by longitudinally symmetrical ribs. U.S. Pat. No. 5,322,056 to Menghi et al. (1994) shows an insole with clusters of bristles extending orthogonally therefrom.

All prior art foot pads and similar devices include symmetrical protrusions that extend orthogonally therefrom. Such protrusions are compressed axially as the person walks, so that they do not bend sideways, and the tip of each protrusion is pressed against the same spot under the user's foot throughout the course of a step. Therefore, such devices merely press into one spot with each step, and therefore provide only relatively minor stimulation.

U.S. Pat. No. 4,249,521 to Gueret (1981) shows a hand held massage pad with rod-shaped protrusions extending orthogonally therefore. Each protrusion has a slanted and concave top surface, so that they are more flexible when brushed in one direction, and less flexible when brushed in the opposite direction. Gueret has no suggestion to use his massage pad as an insole, but even if it were so used, it would be compressed axially by a foot, so that his protrusions will only poke at the bottom of the foot to provide only relatively minor stimulation.

U.S. Pat. No. 5,365,678 to Shibata (1994) shows a midsole including two sheets sealed to form a cavity therebetween. Slanted blades are arranged on one sheet within the cavity. The blades include straight sides that converge to form sharp distal edges. The blades do not contact the foot, so that they cannot provide any stimulation. Shibata does not suggest that his device be adapted so that the blades contact the foot, but even if it were, the sharp edges would tend to dig into the skin when the foot presses on them, so that they will provide only relatively minor stimulation.

OBJECT OF THE INVENTION

Accordingly the primary object of the present invention is to provide a foot pad that provides stimulation to the foot, and to provide such a pad that provides foot stimulation in a unique manner. Other objects are to provide a foot pad that massages the bottom of a foot by rubbing across it in a horizontal direction while the user walks. Further objects of the present invention will become apparent from a consideration of the drawings and ensuing description.

SUMMARY OF THE INVENTION

A massaging foot pad includes a sheet with resilient protrusions arranged on a top surface thereof. The protrusions are horizontally elongated in one direction and slanted in a perpendicular direction. When a foot presses on the protrusions, such as during the downward movement of a walking step, the protrusions bend obliquely in the direction of slanting, so that they rub across the bottom of the foot in a horizontal direction. When the foot releases pressure on the protrusions, such as during the upward movement of the walking step, the protrusions rebound upwardly, and rub the foot in an opposite horizontal direction. The to-and-fro movements of the protrusions provide a foot massage as the user walks.

Figure 1:
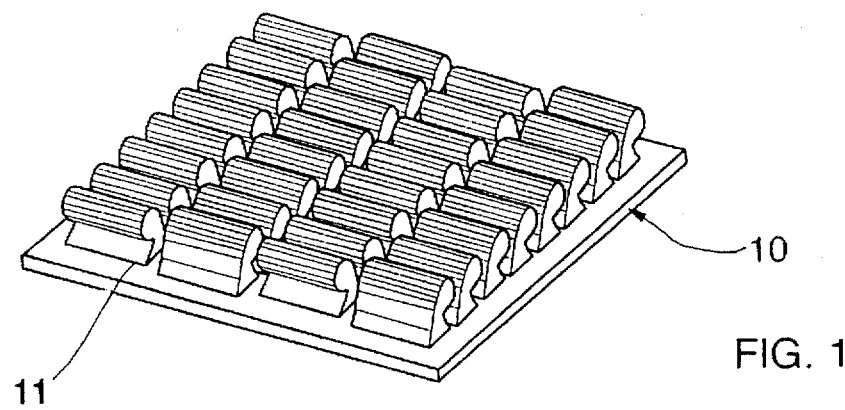
FIG. 1 is a front perspective view of a massaging foot pad in accordance with a first embodiment of the invention.

| Drawing Reference Numerals | |
|---|---|
| 10. Sheet | 11. Protrusions |
| 12. Upper Side | 13. Lower Side |
| 14. Ends | 15. Tip |
| 16. Notch | 20. Sheet |
| 21. Protrusion | 22. Upper Side |
| 23. Lower Side | 24. Ends |
| 25. Tip | 26. Base |
| 30. Sheet | 31. Protrusion |
| 32. Upper Side | 33. Lower Side |
| 34. Ends | 35. Tip |
| 36. Notch | 37. Base |
| 40. Sheet | 41. Protrusion |
| 42. Upper Side | 43. Lower Side |
| 44. Ends | 45. Tip |
| 50. Shoe | 51. Foot |

DESCRIPTION—FIG. 1—FIRST EMBODIMENT

In accordance with a first embodiment of the invention shown in the front perspective view in FIG. 1, a massaging foot pad includes a horizontal sheet 10 (partially shown) with resilient protrusions 11 arranged in rows on a top surface thereof. Each protrusion 11 is horizontally elongated in one direction, and slanted in an orthogonal direction. Adjacent rows of protrusions 11 are slanted in opposite directions. The massaging foot pad is sized and shaped for being placed inside a shoe (not shown) or attached to the top surface of a sandal (not shown).

DESCRIPTION—FIG. 2—SIDE VIEW

Figure 2:
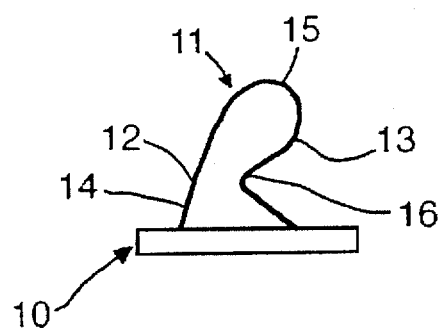
FIG. 2 is a side view of a protrusion of the foot pad of FIG. 1.

A single protrusion 11 is shown in the side view in FIG. 2. It includes an upper side 12 facing obliquely upwardly, a lower side 13 facing obliquely downwardly, opposite ends 14 (one shown) perpendicular to sheet 10, and a thick rounded tip 15. A cutout or notch 16 is arranged on lower side 13, so that protrusion 11 can be easily bent in the direction of the slant. The operation of the foot pad will be explained in conjunction with FIGS. 10–12.

In this embodiment, protrusion 11 is 12 mm long, 4 mm wide, and 5 mm high. The protrusion rows are spaced about 3 mm apart, and have a row-to-row pitch of about 8 mm. The protrusions are preferably made of dense urethane or silicone.

DESCRIPTION—FIG. 3—SECOND EMBODIMENT

In accordance with a second embodiment of the invention shown in the front perspective view in FIG. 1, a massaging foot pad includes a sheet 10 with slanted protrusions 11 arranged in groups of parallel pairs on a top surface thereof. Adjacent pairs of protrusions 11 are arranged orthogonally to each other. The operation of the foot pad will be explained in conjunction with FIGS. 10–12.

Figure 4:
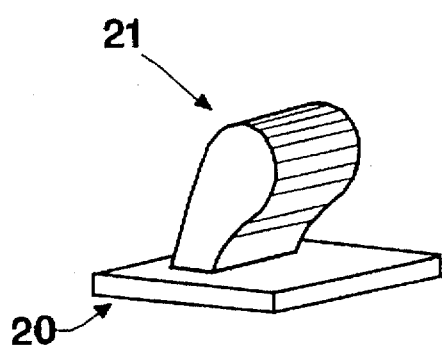
FIG. 4 is a front perspective view of a protrusion in accordance with a third embodiment of the invention.
Figure 5:
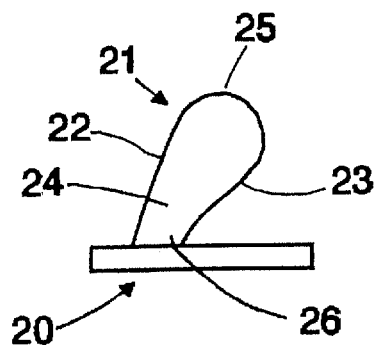
FIG. 5 is a side view of the protrusion of FIG. 4.

DESCRIPTION—FIGS. 4 and 5—THIRD EMBODIMENT

In accordance with a third embodiment of the invention shown in the front perspective view in FIG. 4, a massaging foot pad includes a sheet 20 (partially shown) with an array of resilient protrusions 21 (one shown) arranged on a top surface thereof. Protrusion 21 is horizontally elongated in one direction, and slanted in an orthogonal direction.

As shown in the side view in FIG. 5, protrusion 21 includes an upper side 22 facing obliquely upwardly, a lower side 23 facing obliquely downwardly, opposite ends 24 (one shown) perpendicular to sheet 20, and a rounded tip 25. A base 26 is substantially narrower than tip 25, so that protrusion 21 can be easily bent in the direction of the slant. The operation of the foot pad will be explained in conjunction with FIGS. 10–12.

Figure 6:
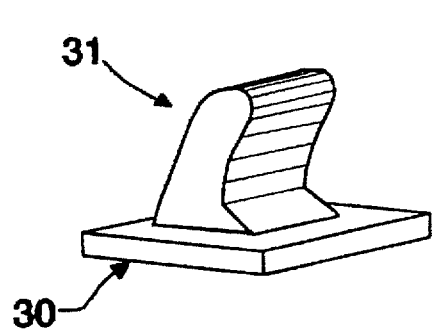
FIG. 6 is a front perspective view of a protrusion in accordance with a fourth embodiment of the invention.
Figure 7:
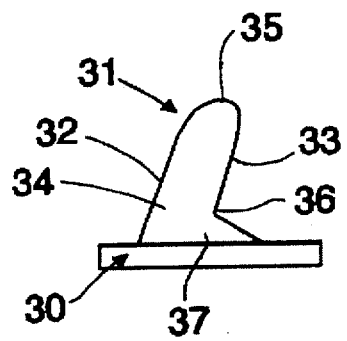
FIG. 7 is a side view of the protrusion of FIG. 6.

DESCRIPTION—FIGS. 6 and 7—FOURTH EMBODIMENT

In accordance with a fourth embodiment of the invention shown in the front perspective view in FIG. 6, a massaging foot pad includes a sheet 30 (partially shown) with an array of resilient protrusions 31 (one shown) arranged on a top surface thereof. Protrusion 31 is horizontally elongated in one direction, and slanted in an orthogonal direction.

As shown in the side view in FIG. 7, protrusion 31 includes an upper side 32 facing obliquely upwardly, a lower side 33 facing obliquely downwardly, opposite ends 34 (one shown) perpendicular to sheet 20, and a rounded tip 35. A base 37 is substantially wider than tip 35. A notch 36 is arranged on lower side 33, so that protrusion 31 can be easily bent in the direction of the slant. The operation of the foot pad will be explained in conjunction with FIGS. 10–12.

Figure 8:
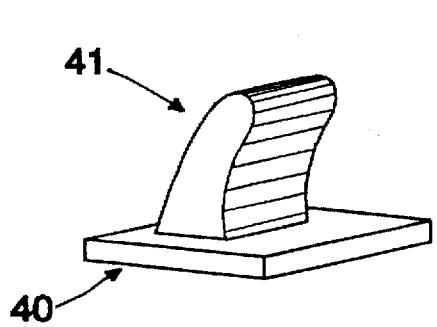
FIG. 8 is a front perspective view of a protrusion in accordance with fifth embodiment of the invention.
Figure 9:
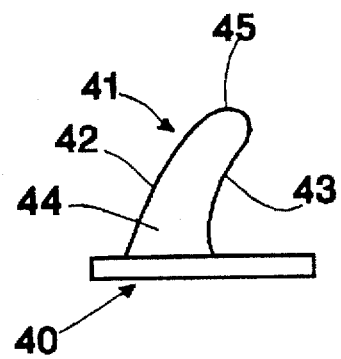
FIG. 9 is a side view of the protrusion of FIG. 8.

DESCRIPTION—FIG. 8 and 9—FIFTH EMBODIMENT

In accordance with a fifth embodiment of the invention shown in the front perspective view in FIG. 8, a massaging foot pad includes a sheet 40 (partially shown) with an array of resilient protrusions 41 (one shown) arranged on a top surface thereof. Protrusion 41 is horizontally elongated in one direction, and slanted in an orthogonal direction.

As shown in the side view in FIG. 9, protrusion 41 includes a convex upper side 42 facing obliquely upwardly, a concave lower side 43 facing obliquely downwardly, opposite ends 44 (one shown) perpendicular to sheet 40, and a rounded tip 45. Upper and lower sides 42 and 43, respectively, are curved in the direction of the slant, so that protrusion 41 can be easily bent in the same direction. The operation of the foot pad will be explained in conjunction with FIGS. 10–12.

Figure 10:
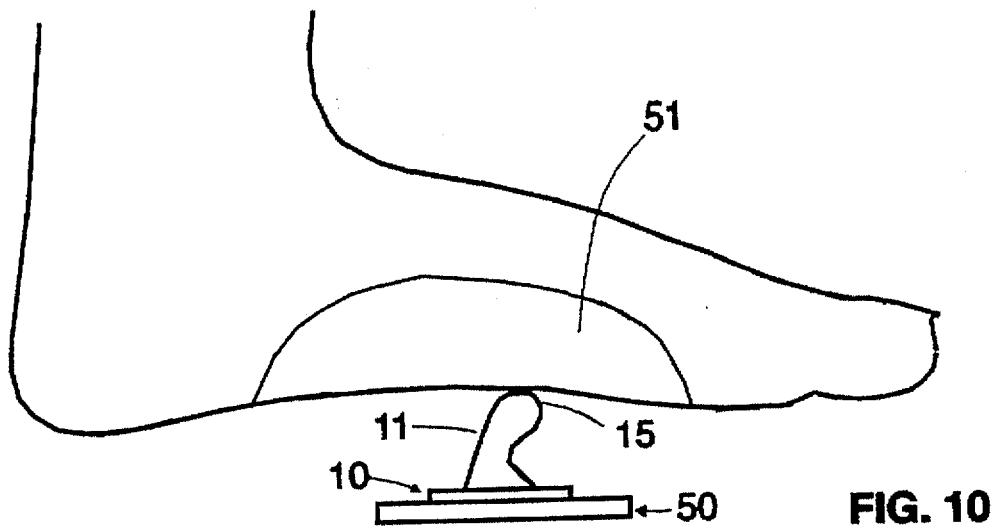
FIG. 10 is a side view of the protrusion in use.
Figure 11:
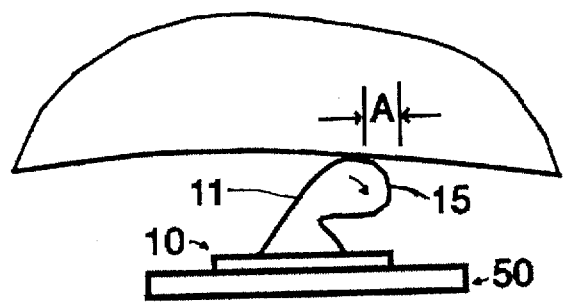
FIG. 11 is a side view of the protrusion in use.
Figure 12:
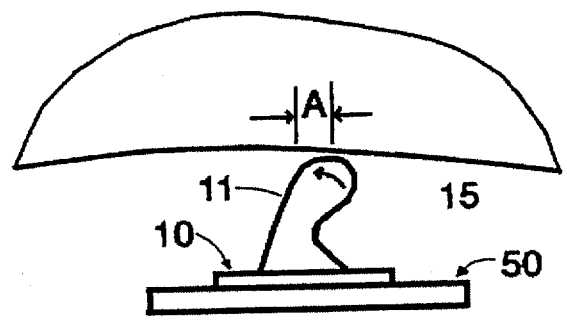
FIG. 12 is a side view of the protrusion in use.

OPERATION—FIGS. 10 to 12

Protrusions 11, 21 (FIG. 4), 31 (FIG. 6), and 41 (FIG. 8) of the massaging foot pad operate in a substantially identical manner, which is illustrated with a single protrusion 11 in FIGS. 10 to 12.

The massaging foot pad is shown positioned in the sole of a shoe 50 (partially shown) and a foot 51 (partially shown), in an at-rest condition in FIG. 10. Tip 15 is in contact with the bottom of foot 51. Before the weight of the standing person presses downwardly on the foot pad, each protrusion remains fully upright The operation of the massaging foot pad during the downward movement of a walking step is shown in FIG. 11. Foot 51 presses downwardly, as indicated by one arrow, and bends protrusion 11 obliquely in the direction of its slant, as indicated by another arrow. Tip 15 thus moves horizontally across the bottom of foot 51 over a distance A. Being rounded, some of tips 15 rub across foot 51 easily. Other tips will grip the skin at the point of contact and move the skin horizontally, so that the underside of the skin rubs against the muscle tissue underneath.

The operation of the massaging foot pad during the upward movement of a walking step is shown in FIG. 12. Foot 51 moves upwardly slightly within shoe 50, as indicated by one arrow, so that protrusion 11 rebounds obliquely in a direction opposite to its slant, as indicated by another arrow. Tip 15 thus rubs against or moves with the skin horizontally across the bottom of foot 51 over the same distance A in the opposite direction. The to-and-fro movements of protrusion 11 provide a horizontal rubbing action or massage on the bottom of foot 51 as the user walks.

Figure 3:
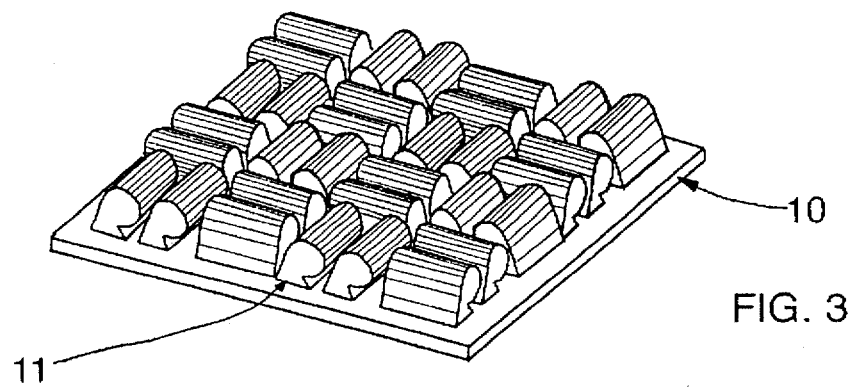
FIG. 3 is a front perspective view of a massaging foot pad in accordance with a second embodiment of the invention.

The arrangement shown in FIG. 1 provides rubbing or massaging action in alternating opposite directions between the rows of protrusions 11. The arrangement shown in FIG. 3 provides rubbing action in orthogonal directions between each group of protrusions 11.

In either case, the to-and-fro or horizontal rubbing action provides a desirable, stimulating massage to the bottom of the user's feet, increasing blood flow, lymphatic action, and providing neural stimulation. This tends to relieve foot strain, fatigue, and soreness, and enables the user to walk or run farther.

SUMMARY, RAMIFICATIONS AND SCOPE

Accordingly, the reader will see that I have provided a foot pad that can be installed in a shoe or sandal to provide a highly beneficial massage to the bottom of the foot as the user walks.

Although the above descriptions are specific, they should not be considered as limitations on the scope of the invention, but only as examples of the embodiments. Many other ramifications and variations are possible within the teachings of the invention. For example, the foot pad can be made in a variety of shapes and sizes for fitting different types and sizes of shoes and sandals. It can be provided as a built-in insole of any footwear. It can be placed on the floor for massaging a bare foot. The notch can be arranged on the upper side of the protrusion. Various other materials, shapes, and arrangements of the protrusions can be used. Therefore, the reader is requested to determine the scope of the invention by the appended claims and their legal equivalents, and not by the examples given.

I claim:

1. A method of massaging a foot, comprising;

positioning a sheet horizontally under a foot, said sheet having a plurality of adjacent groups of foot-massaging protrusions, each group having a plurality of resilient, bendable protrusions, each protrusion having a base attached on top of said sheet and a tip for engaging a bottom of said foot, said protrusions of a first of said adjacent groups being slanted in a predetermined direction and said protrusions of a second of said adjacent groups being slanted in a different predetermined direction so that said first and second adjacent groups define a predetermined orientation with respect to one another, said plurality of adjacent groups defining a repeating pattern of said predetermined orientation, each protrusion including an upper side facing obliquely upward and a lower side facing obliquely downward;

alternately pressing said foot downwardly and lifting it upwardly on said sheet so that when said foot moves downward, each protrusion bends downwardly and said tip easily rubs horizontally across said bottom of said foot in one direction, and when said foot lifts upwardly, each protrusion rebounds upwardly, and said tip rubs horizontally across said bottom of said foot in a direction opposite to said one direction, whereby said bottom of said foot will be massaged with a back-and-forth horizontal movement by said tips when foot moves upwardly and downwardly.

2. The method of massaging a foot of claim 1 wherein each protrusion is elongated in said predetermined direction and has a rounded tip.

3. The method of massaging a foot of claim 1 wherein said base of each protrusion is substantially narrower than said tip.

4. The method of massaging a foot of clam 1 wherein said upper side of each protrusion is convex, and said lower side of each protrusion is concave, so that each protrusion is easily bent.

5. The method of massaging a foot of claim 1 wherein said plurality of adjacent groups of foot-massaging protrusions are arranged as rows of protrusions, said protrusions in each row being slanted in one direction, and adjacent rows of said protrusions being slanted in opposite direction.

6. The method of massaging a foot of claim 1 wherein said plurality of adjacent groups of foot-massaging protrusion are arranged as parallel pairs protrusions, said protrusions in each pair being slanted in one direction, and said protrusions in adjacent pairs being slanted in orthogonal directions.

7. The method of massaging a foot of claim 1, further including a notch on each protrusion.

8. The method of massaging a foot of claim 7 wherein said tip of each protrusion is substantially narrower than said base.

9. The method of massaging a foot of claim 7 wherein said notch is arranged on said lower side of each protrusion.

10. The method of massaging a foot of claim 1 wherein said sheet is positioned in an article of footwear, so that said massaging alternately pressing said foot downwardly and lifting it upwardly on said sheet will occur when a wearer of said footwear walks.

11. A massaging foot pad, comprising;

a sheet for being positioned horizontally under a foot;

a plurality of resilient, bendable protrusion arranged in a plurality of adjacent groups of foot-massaging protrusion, each protrusion having a base attached on top of said sheet and a tip for engaging a bottom of said foot, each protrusion including an upper side facing obliquely upwardly and lower side facing obliquely downwardly; and said protrusions being slanted in at least two predetermined directions so that a first group of said protrusions slants in a direction different than protrusions in a second group so that said first and second groups define a predetermined orientation with respect to one another, said plurality of adjacent groups defining a repeating pattern of said predetermined orientation, said protrusions being shaped, made, and positioned so that when said foot presses downwardly on said protrusions, each protrusion bends downwardly, and said tips of said first group of protrusions rub horizontally across said bottom of said foot in a first direction, said tips of said second group of protrusions rub horizontally across said bottom of said foot in a second direction different to said first direction, and when said foot lifts upwardly, said protrusions rebound upwardly, and said tips of said group of protrusions rub horizontally across said bottom of said foot in said second direction, said tips of said second group of protrusions rub horizontally across said bottom of said foot in said first direction, whereby said protrusions of said plurality of adjacent groups will massage said bottom of said foot in alternate and different to-and-fro horizontal motions.

12. The massaging foot pad of claim 11 wherein said tip of each protrusion is rounded for easily rubbing across said bottom of said foot.

13. The massaging foot pad of claim 11 wherein said upper side of each protrusion is convex, and said lower side of each protrusion is concave, so that each protrusion is easily bent.

14. The massaging foot pad of claim 11 wherein said tip of each protrusion is substantially narrower than said base.

15. The massaging foot pad of claim 11 wherein said protrusions of said plurality of adjacent groups are arranged as a plurality of rows, said protrusions in each row being slanted in one direction, and adjacent rows of said protrusions being slanted in opposite directions.

16. The massaging foot pad of claim 11 wherein said protrusions of said plurality of adjacent groups are arranged as a plurality of parallel pairs, said protrusions in each pair being slanted in one direction, and said protrusions in adjacent pairs being slanted in orthogonal directions.

17. The massaging foot pad of claim 11, further including a notch on each protrusion.

18. The massaging foot pad of claim 17 wherein said tip of each protrusion is substantially narrower than said base.

19. The massaging foot pad of claim 17 wherein said notch is arranged on said lower side of each protrusion.

* * * * *

UNITED STATES PATENT AND TRADEMARK OFFICE
CERTIFICATE OF CORRECTION

PATENT NO.  : 5,735,804
DATED       : April 7, 1998
INVENTOR(S) : Erik Chan

It is certified that error appears in the above-identified patent and that said Letters Patent is hereby corrected as shown below:

Col. 1, line 36, change "therefore" to --therefrom--.

Signed and Sealed this

Second Day of June, 1998

Attest:

BRUCE LEHMAN

*Attesting Officer*  *Commissioner of Patents and Trademarks*